(12) United States Patent
Shaw

(10) Patent No.: US 10,610,395 B2
(45) Date of Patent: Apr. 7, 2020

(54) SLEEVES FOR EXPANDABLE MEDICAL DEVICES

(71) Applicant: W. L. Gore & Associates, Inc., Newark, DE (US)

(72) Inventor: Edward E. Shaw, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 411 days.

(21) Appl. No.: 15/430,263

(22) Filed: Feb. 10, 2017

(65) Prior Publication Data
US 2017/0151079 A1   Jun. 1, 2017

Related U.S. Application Data

(63) Continuation of application No. 14/061,595, filed on Oct. 23, 2013, now Pat. No. 9,592,143, which is a continuation of application No. 13/295,861, filed on Nov. 14, 2011, now abandoned.

(60) Provisional application No. 61/414,253, filed on Nov. 16, 2010.

(51) Int. Cl.
| A61F 2/97 | (2013.01) |
| A61F 2/07 | (2013.01) |
| A61F 2/82 | (2013.01) |
| A61F 2/95 | (2013.01) |
| A61F 2/954 | (2013.01) |

(Continued)

(52) U.S. Cl.
CPC ................. *A61F 2/97* (2013.01); *A61F 2/07* (2013.01); *A61F 2/82* (2013.01); *A61F 2/954* (2013.01); *A61F 2/958* (2013.01); *A61F 2002/061* (2013.01); *A61F 2002/9511* (2013.01); *A61F 2250/0067* (2013.01); *A61F 2250/0098* (2013.01)

(58) Field of Classification Search
CPC .... A61F 2/95; A61F 2/954; A61F 2/97; A61F 2002/061; A61F 2002/9511; A61F 2250/0067; A61F 2250/0098
See application file for complete search history.

(56) References Cited

U.S. PATENT DOCUMENTS 5,873,906 A * 2/1999 Lau ........................... A61F 2/07
                                                    128/898
6,030,414 A    2/2000 Taheri
(Continued)

FOREIGN PATENT DOCUMENTS

JP      2003250907 A     9/2003
WO   WO-1998027894 A1   7/1998
(Continued)

*Primary Examiner* — Julie A Szpira

(57) ABSTRACT

The present disclosure describes treatment of the vasculature of a patient with an expandable implant. The implant is constrained to a reduced delivery profile for delivery within the vasculature by at least one sleeve. The implant may be constrained to other diameters, such as an intermediate configuration having a diameter larger than the delivery profile and smaller than the deployment diameter. The sleeves may be expanded, allowing for expansion of the diameter of the expandable implant, by disengaging a coupling member from the sleeve or sleeves from outside of the body of the patient. The expandable implant may comprise a number of side branch fenestrations or fenestratable portions.

18 Claims, 8 Drawing Sheets

(51) Int. Cl.
*A61F 2/06* (2013.01)
*A61F 2/958* (2013.01)

(56) References Cited

U.S. PATENT DOCUMENTS

| | | | |
|---|---|---|---|
| 6,224,627 B1* | 5/2001 | Armstrong | A61F 2/82 623/1.13 |
| 6,315,792 B1 | 11/2001 | Armstrong et al. | |
| 6,338,724 B1 | 1/2002 | Dossa | |
| 6,352,553 B1 | 3/2002 | Van Der Burg | |
| 6,599,316 B2 | 7/2003 | Vardi et al. | |
| 2002/0029077 A1 | 3/2002 | Leopold et al. | |
| 2003/0167083 A1 | 9/2003 | Lashinski et al. | |
| 2003/0236566 A1 | 12/2003 | Heuser | |
| 2004/0172121 A1 | 9/2004 | Eidenschink | |
| 2004/0251668 A1 | 12/2004 | Schneider | |
| 2005/0085845 A1 | 4/2005 | Hilaire et al. | |
| 2005/0182476 A1 | 8/2005 | Hartley et al. | |
| 2005/0187602 A1 | 8/2005 | Eidenschink | |
| 2005/0273151 A1 | 12/2005 | Fulkerson | |
| 2006/0004433 A1 | 1/2006 | Greenberg et al. | |
| 2006/0015171 A1* | 1/2006 | Armstrong | A61B 17/12022 623/1.12 |
| 2007/0083215 A1 | 4/2007 | Hamer et al. | |
| 2007/0168020 A1* | 7/2007 | Brucker | A61F 2/856 623/1.35 |
| 2007/0299494 A1 | 12/2007 | Zukowski | |
| 2008/0269866 A1* | 10/2008 | Hamer | A61F 2/07 623/1.11 |
| 2010/0049298 A1 | 2/2010 | Hamer et al. | |
| 2012/0109279 A1 | 5/2012 | Mayberry et al. | |
| 2012/0130473 A1* | 5/2012 | Norris | A61F 2/97 623/1.12 |
| 2012/0130475 A1 | 5/2012 | Shaw | |
| 2014/0025162 A1 | 1/2014 | Hamer et al. | |

FOREIGN PATENT DOCUMENTS

| | | |
|---|---|---|
| WO | 1999/065420 A1 | 12/1999 |
| WO | WO-2000033770 A2 | 6/2000 |
| WO | WO-2000074595 A1 | 12/2000 |
| WO | WO-2005025458 A1 | 3/2005 |
| WO | 2005/070336 A1 | 8/2005 |
| WO | WO-2005094726 A1 | 10/2005 |
| WO | WO-2007001519 A1 | 1/2007 |
| WO | WO-2008133802 A1 | 6/2008 |
| WO | WO-2012065080 A2 | 5/2012 |

* cited by examiner

SLEEVES FOR EXPANDABLE MEDICAL DEVICES

CROSS REFERENCE TO RELATED APPLICATION

This application is a continuation application to U.S. patent application Ser. No. 14/061,595, filed Oct. 23, 2013, which is a continuation application to U.S. patent application Ser. No. 13/295,861, filed Nov. 14, 2011, now abandoned, which claims priority to U.S. Provisional Patent Application No. 61/414,253, entitled "SEGMENTED CONSTRAINING SLEEVES FOR EXPANDABLE MEDICAL DEVICES" filed Nov. 16, 2010, all of which are hereby incorporated by reference in their entireties.

BACKGROUND

Field

The present disclosure relates generally to the transcatheter delivery and remote deployment of implantable medical devices.

Discussion of the Related Art

Endoluminal devices used to treat a treatment area of the vasculature of a patient are typically delivered via a catheter assembly. Such endoluminal devices may comprise, for example, expandable implants. One common type of expandable implant is the stent graft. Stent grafts may have a reduced diameter, collapsed configuration for delivery to the patient's vasculature, then be expanded once the treatment area of the vasculature is reached. Stent grafts may be constrained in the collapsed configuration by a biocompatible sleeve.

While the use of such sleeves provides a convenient way to constrain the stent graft, sleeves may give rise to other problems or issues. For example, it may be difficult to position a stent graft that is constrained by a biocompatible sleeve for implanting within the treatment area of the vasculature. Further, it may be difficult to remove or expand the sleeve to allow for expansion of the stent graft. Finally, orienting or locating a sleeve-constrained stent graft after it has been expanded may be difficult. These issues can be exaggerated when a sleeve-constrained stent graft is configured with side branch fenestrations (or side branch portals) or fenestratable portions configured for the attachment of side branches.

Therefore, devices, systems and methods that facilitate improved preparation of a sleeve-constrained expandable implant for delivery, accurate delivery of the implant, and correct orientation and position of the implant would be useful and desirable.

BRIEF DESCRIPTION OF THE DRAWINGS

The accompanying drawings are included to provide a further understanding of the disclosure and are incorporated in and constitute a part of this specification, illustrate embodiments of the disclosure, and together with the description serve to explain the principles of the disclosure, wherein.

DETAILED DESCRIPTION OF THE ILLUSTRATED EMBODIMENTS

While the present disclosure describes a number of embodiments, it will be understood that the disclosure is not limited to these embodiments. Instead, it is intended to cover all alternatives, modifications, and equivalents as may be included within the spirit and scope of the disclosure as described and claimed.

Various embodiments of the present disclosure comprise a catheter assembly configured to deliver an expandable implant to a treatment area of the vasculature of a patient. In accordance with embodiments of the disclosure, an expandable implant is constrained by one or more sleeves. When the sleeves are expanded or removed, one or more target portions of the expandable implant can be exposed. In various embodiments, the target portion or portions comprise side branch fenestrations or fenestratable portions. Such target portions may be revealed between adjacent sleeves or between the edges of a single sleeve.

Figure 1:
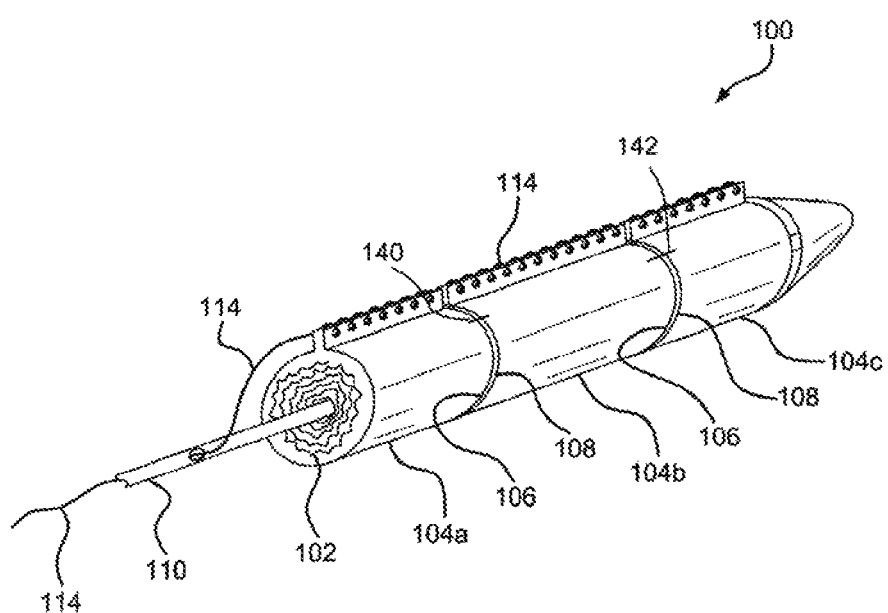
FIG. 1 is a perspective view of a catheter assembly having a medical device constrained in a delivery profile by a plurality of tubular sleeves.

With initial reference to FIG. 1, a catheter assembly 100 in accordance with the present disclosure comprises an expandable implant 102. Expandable implant 102 may comprise any endoluminal device suitable for delivery to the treatment area of a vasculature. Such devices may include, for example, stents, grafts, and stent grafts.

In various embodiments, expandable implant 102 comprises a stent graft. Conventional stent grafts are designed to dilate from the diameter of the delivery profile, through a range of intermediary diameters, up to a maximal, predetermined functional diameter, and generally comprise one or more stent components with one or more graft members displaced over and/or under the stent.

In various embodiments, expandable implant 102 comprises one or more stent components made of nitinol and a graft member made of ePTFE. However, and as discussed below, any suitable combination of stent component(s) and graft member(s) is within the scope of the present disclosure.

For example, stent components can have various configurations such as, for example, rings, cut tubes, wound wires (or ribbons) or flat patterned sheets rolled into a tubular form. Stent components can be formed from metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol and biologically derived materials such as bovine arteries/veins, pericardium and collagen. Stent components can also comprise bioresorbable materials such as poly(amino acids), poly(anhydrides), poly(caprolactones), poly(lactic/glycolic acid) polymers, poly(hydroxybutyrates) and poly(orthoesters). Any expandable stent component configuration which may be delivered by a catheter is in accordance with the present disclosure.

Moreover, potential materials for graft members include, for example, expanded polytetrafluoroethylene (ePTFE), polyester, polyurethane, fluoropolymers, such as perfouorelastomers and the like, polytetrafluoroethylene, silicones, urethanes, ultra high molecular weight polyethylene, aramid fibers, and combinations thereof. Other embodiments for a graft member material can include high strength polymer fibers such as ultra high molecular weight polyethylene fibers (e.g., Spectra®, Dyneema Purity®, etc.) or aramid fibers (e.g., Technora®, etc.). The graft member may include a bioactive agent. In one embodiment, an ePTFE graft includes a carbon component along a blood contacting surface thereof. Any graft member which may be delivered by a catheter is in accordance with the present disclosure.

In various embodiments, a stent component and/or graft member may comprise a therapeutic coating. In these embodiments, the interior or exterior of the stent component and/or graft member can be coated with, for example, a CD34 antigen. Additionally, any number of drugs or therapeutic agents may be used to coat the graft member, including, for example heparin, sirolimus, paclitaxel, everolimus, ABT-578, mycophenolic acid, tacrolimus, estradiol, oxygen free radical scavenger, biolimus A9, anti-CD34 antibodies, PDGF receptor blockers, MMP-1 receptor blockers, VEGF, G-CSF, HMG-CoA reductase inhibitors, stimulators of iNOS and eNOS, ACE inhibitors, ARBs, doxycycline, and thalidomide, among others.

In various embodiments, expandable implant 102 may comprise a radially collapsed configuration suitable for delivery to the treatment area of the vasculature of a patient. Expandable implant 102 may be constrained in a radially collapsed configuration and mounted onto a delivery device such as catheter shaft 110. The diameter of the expandable implant 102 in the collapsed configuration is small enough for the implant to be delivered through the vasculature to the treatment area. In various embodiments, the diameter of the collapsed configuration is small enough to minimize the crossing profile of catheter assembly 100 and reduce tissue damage to the patient. In the collapsed configuration, the expandable implant 102 may be guided by catheter shaft 110 through the vasculature.

In various embodiments, expandable implant 102 may comprise a radially expanded configuration suitable for implanting the device in the treatment area of a patient's vasculature. In the expanded configuration, the diameter of expandable implant 102 may be approximately the same as the vessel to be repaired. In other embodiments, the diameter of expandable implant 102 in the expanded configuration may be slightly larger than the vessel to be treated to provide a traction fit within the vessel.

In various embodiments, expandable implant 102 may comprise a self-expandable device, such as a self-expandable stent graft. Such devices dilate from a radially collapsed configuration to a radially expanded configuration when unrestrained. In other embodiments, expandable implant 102 may comprise a device that is expanded with the assistance of a secondary device such as, for example, a balloon. In yet other embodiments, catheter assembly 100 may comprise a plurality of expandable implants 102. The use of a catheter assembly with any number of expandable implants is within the scope of the present disclosure.

Various medical devices in accordance with the disclosure comprise a sleeve or multiple sleeves. The sleeve or sleeves may constrain an expandable implant device in a collapsed configuration for endoluminal delivery of the implant to a treatment portion of the vasculature of a patient. For the purposes of the disclosure, the term "constrain" may mean (i) to limit the expansion, either through self-expansion or assisted by a device, of the diameter of an expandable implant or (ii) to cover or surround but not otherwise restrain an expandable implant (e.g., for storage or biocompatibility reasons and/or to provide protection to the expandable implant and/or the vasculature).

After deployment, the sleeve or sleeves may be removed in order to allow the expandable implant to expand to its functional diameter and achieve the desired therapeutic outcome. The sleeve or sleeves can remain implanted while not interfering with the expandable implant.

Figure 6:
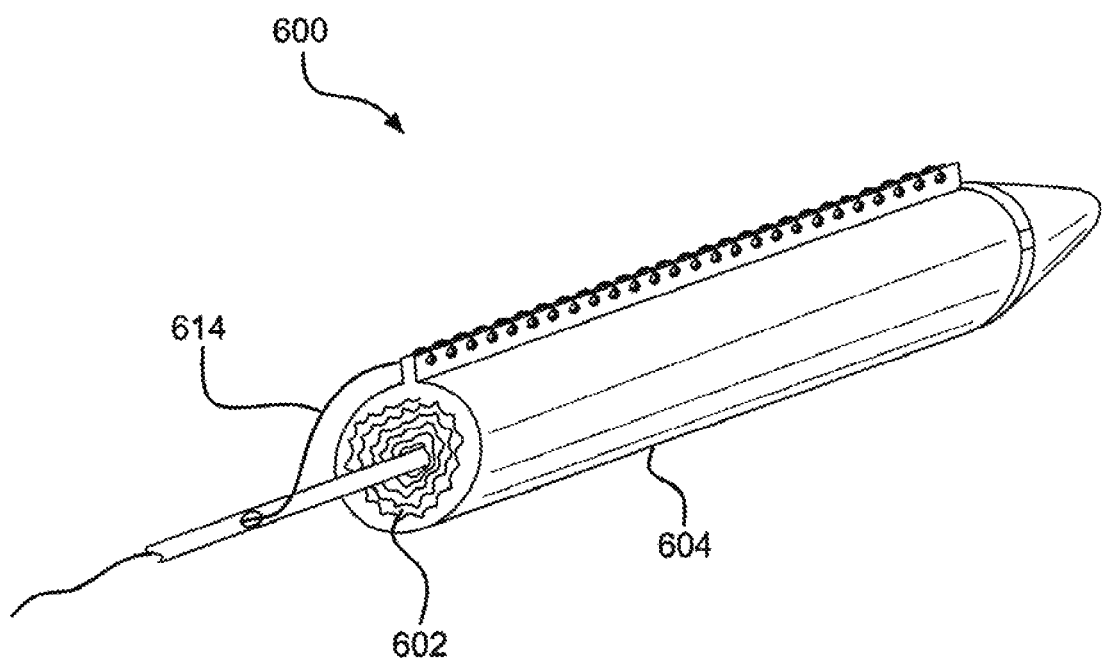
FIG. 6 is a perspective view of a catheter assembly having a medical device constrained in a delivery profile by a tubular sleeve.

In various embodiments, an expandable implant is constrained by a single sleeve which circumferentially surrounds the expandable implant. For example, with reference to FIG. 6, catheter assembly 600 comprises a sleeve 604. In various embodiments, sleeve 604 circumferentially surrounds expandable implant 602 and constrains it in a collapsed configuration, in which the diameter is less than the diameter of the unconstrained implant. For example, sleeve 604 may constrain expandable implant 602 in a collapsed configuration for delivery within the vasculature.

In other embodiments, an expandable implant is constrained by a plurality of sleeves which circumferentially surround the expandable implant. For example, with reference to FIG. 1, catheter assembly 100 comprises sleeves 104a, 104b, and 104c. Each sleeve 104 is distinct and separate from the other two sleeves, and each concentrically surrounds a portion of expandable implant 102.

In various embodiments, sleeves 104a, 104b, and 104c may be coupled to each other, such as, by adhesive bonding, tethering, or any other form of coupling. For example, with reference to FIG. 1, sleeves 104a, 104b, and 104c may be coupled together by tethers 140 and 142 such that sleeves 104a, 104b, and 104c act as one individual sleeve. Tethers 140 and 142 may comprise any of the suitable materials of the present disclosure, such as the same material of which sleeves 104a, 104b, and 104c are made. Indeed, in some embodiments, a single sleeve may be cut or perforated in such a manner as to create individual sleeves 104a, 104b, and 104c, but leaving tethers 140 and 142. In some embodiments, described in greater detail below, lateral openings are cut in a single sleeve such that the single sleeve acts as multiple sleeves (e.g., by relatively large sizing of lateral openings, etc.). In various configurations, sleeves 104a, 104b, and 104c being coupled together in some manner may facilitate easier removal of the sleeves after deployment of expandable implant 102 and/or or ensure sleeves 104a, 104b, and 104c stay implanted as one individual sleeve.

In such configurations, each distinct sleeve may be formed as individual sleeves, or may be created by forming a single sleeve around an expandable implant and creating individual sleeves from the single sleeve by, for example, cutting the single sleeve into individual sleeves.

Figure 3:
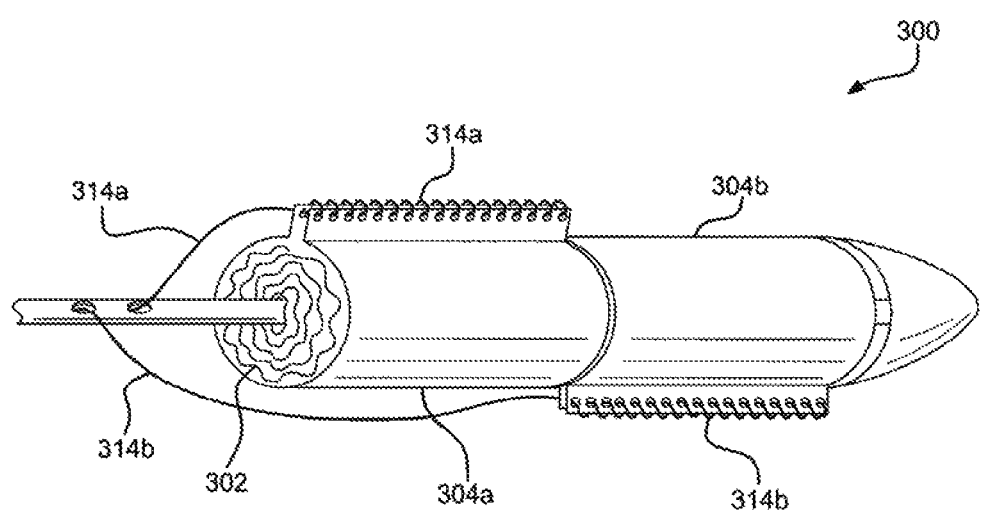
FIG. 3 is a perspective view of a catheter assembly having a medical device constrained in a delivery profile by angularly displaced sleeves.

As a further example, with reference to FIG. 3, catheter assembly 300 comprises sleeves 304a and 304b. Each sleeve 304 is distinct and separate from the other sleeve, and each concentrically surrounds a portion of expandable implant 302.

In various embodiments, sleeves can be tubular and serve to constrain an expandable implant. In such configurations, sleeves are formed from a sheet of one or more materials wrapped or folded about the expandable implant. In the case where multiple sleeves are used to constrain an expandable implant, each sleeve can comprise at least one sleeve end adjacent to another sleeve end. While the illustrative embodiments herein are described as comprising one or more tubular sleeves, sleeves of any non-tubular shape that corresponds to an underlying expandable implant or that are otherwise appropriately shaped for a given application are also within the scope of the present disclosure.

In various embodiments, sleeves are formed by wrapping or folding the sheet of material(s) such that two parallel edges of the sheet are substantially aligned. Said alignment may or may not be parallel to or coaxial with the catheter shaft of a catheter assembly. In various embodiments, the edges of the sheet of material(s) do not contact each other.

In various embodiments, the edges of the sheet of material(s) do contact each other and are coupled with a coupling member, as described below, an adhesive, etc. In various other embodiments, the edges of the sheet of material(s) are aligned so that the edges of the same side of the sheet or sheets (e.g., the front or back of the sheet) are in contact with each other. In still other embodiments, the edges of opposite sides of the sheet of material(s) are in contact with each other, such that the edges overlap each other, such that a portion of one side of the sheet is in contact with a portion of the other side. Said another way, the front of the sheet may overlap the rear of the sheet, or vice versa.

In various embodiments, sleeves comprise materials similar to those used to form a graft member. For example, a precursor flexible sheet used to make the sleeve can be formed from a flattened, thin wall ePTFE tube. The thin wall tube can incorporate "rip-stops" in the form of longitudinal high strength fibers attached or embedded into the sheet or tube wall.

The sheet of material(s) used to form the sleeve(s) may comprise a series of openings, such that the openings extend from one edge of the sheet to the other. In such configurations, a coupling member can be woven or stitched through the series of openings in the sheet of material(s), securing each of the two edges together and forming a tube.

In various embodiments, the coupling member may comprise a woven fiber. In other embodiments, the coupling member may comprise a monofilament fiber. Any type of string, cord, thread, fiber, or wire which is capable of maintaining a sleeve in a tubular shape is within the scope of the present disclosure.

In various embodiments, a single coupling member may be used to constrain the diameter of one or more sleeves. For example, with reference to FIG. 6, a coupling member 614 is woven through openings in a single sleeve 604 to maintain the configuration of sleeve 604 around expandable implant 602. In another example, with reference to FIG. 1, a single coupling member 114 is woven through openings in a plurality of sleeves 104a, 104b, and 104c.

In other embodiments, multiple coupling members may be used to constrain the diameter of one or more sleeves. For example, with reference to FIG. 3, coupling members 314a and 314b are used to maintain the configuration of sleeves 304a and 304b, respectively, around expandable implant 302. The use of any number of coupling members in conjunction with a single sleeve or any number of sleeves is within the scope of the present disclosure.

In various embodiments, once a suitable expandable implant is in a collapsed configuration, the expandable implant may be deployed within the vasculature of a patient. An expandable implant in a collapsed configuration may be introduced to a vasculature and directed by a catheter assembly to a treatment area of the vasculature. Once in position in the treatment area of the vasculature, the expandable implant may be expanded to an expanded configuration.

In various embodiments, when the expandable implant is in position within the vasculature, the coupling member or members can be disengaged from the sleeve or sleeves from outside of the body of the patient, which allows the sleeve(s) to open and the expandable implant to expand. As discussed above, the expandable implant may be self-expanding, or the implant may be expanded by a device, such as a balloon.

The coupling member or members may be disengaged from the sleeve or sleeves by a mechanical mechanism operated from outside of the body of the patient. For example, the member or members may be disengaged by applying sufficient tension to the member or members. In another example, a dial or rotational element may be attached to the coupling member or members outside of the body. Rotation of the dial or rotational element may provide sufficient tension to disengage the coupling member or members.

In other configurations, coupling member or members may be disengaged by non-mechanical mechanisms, such as, for example, dissolution, by providing ultrasonic energy. In such configurations, sufficient ultrasonic energy is provided to coupling member or members to disengage them from the sleeve or sleeves.

In various embodiments, disengaging a single coupling member which closes a single sleeve from the sleeve allows the expandable device to be expanded. For example, with reference to FIG. 6, catheter assembly 600 may be used to deliver an implant expandable implant 602 to a treatment area of a vasculature. Expandable implant 602 has a collapsed configuration for delivery, and sleeve 604 circumferentially surrounds expandable implant 602 and is held closed by coupling member 614. Once expandable implant 602 is in position relative to the treatment area, coupling member 614 is disengaged from sleeve 604 and sleeve 604 is released, allowing expandable implant 602 to expand to a larger diameter.

In other embodiments, a single coupling member closing a plurality of sleeves is disengaged from the plurality of sleeves to allow an expandable device to be expanded. For example, with reference to FIG. 1, catheter assembly 100 comprises a plurality of sleeves 104 surrounding expandable implant 102. Each sleeve 104 is oriented on the longitudinal axis of catheter shaft 110 such that the portion of each sleeve 104 stitched together by a single coupling member 114 is substantially aligned with each other. However, any degree of relative angular displacement between the plurality of sleeves 304 is within the scope of the present disclosure.

Upon disengagement of coupling member 114 from the most distal sleeve 104c, the portion of expandable implant 102 constrained by sleeve 104c may expand to a larger diameter. As previously discussed, expandable implant 102 may be self-expandable, or may expand with the aid of a device such as a balloon.

Coupling member 114 is then further disengaged, allowing the portion of expandable implant 102 constrained by the next most distal sleeve 104b to expand to a larger diameter. The remainder of coupling member 114 may then be disengaged, and the next most distal sleeve 104a is opened, allowing expandable implant 102 to expand to its expanded configuration the along the remainder of its longitudinal axis. Although the disengagement of coupling member 114 is described as beginning at the distal end of expandable implant 102 and progressing toward the proximal end, any order of disengagement of coupling member or members from a sleeve or multiple sleeves is within the scope of the present disclosure, for example proximal to distal, middle to ends, ends to middle, etc.

In other embodiments, multiple coupling members are used in conjunction with a single sleeve or multiple sleeves. For example, with reference to FIG. 3, catheter assembly 300 comprises at least two sleeves 304a and 304b. Sleeves 304a and 304b are held closed by coupling members 314a and 314b, respectively. In various embodiments, sleeves 304a and 304b may be oriented such that the portions of the sleeves secured by coupling members 314a and 314b are angularly displaced relative to each other by about 180 degrees. In other embodiments, the portions of the sleeves secured by coupling members 314a and 314b are angularly displaced relative to each other by more than about zero degrees and less than about 180 degrees. Any degree of relative angular displacement between the plurality of sleeves 304 is within the scope of the present disclosure.

In such configurations as illustrated in FIG. 3, coupling members 314a and 314b may be disengaged separately to open sleeves 304a and 304b. Once both sleeves 304 have been opened, expandable implant 302 may be expanded to an expanded configuration.

In various embodiments of the present disclosure, an expandable implant may further comprise an intermediate configuration. In the intermediate configuration, the diameter of the expandable implant is constrained in a diameter smaller than the expanded configuration and larger than the collapsed configuration. In such embodiments, the expandable implant may be expanded from the collapsed configuration to the intermediate configuration once the implant has been delivered near the treatment area of the vasculature of a patient. The intermediate configuration may, among other things, assist in properly orienting and locating the expandable implant within the treatment area of the vasculature.

In various embodiments, an expandable implant may be concentrically surrounded by at least two sleeves having different diameters. In such configurations, one or more primary sleeves constrain the expandable implant in a delivery profile. Once the primary sleeve is opened, one or more secondary sleeves constrain the expandable implant in an intermediate configuration. As discussed above, the expandable implant may be self-expanding, or the implant may be expanded by a device, such as a balloon.

Figure 7A:
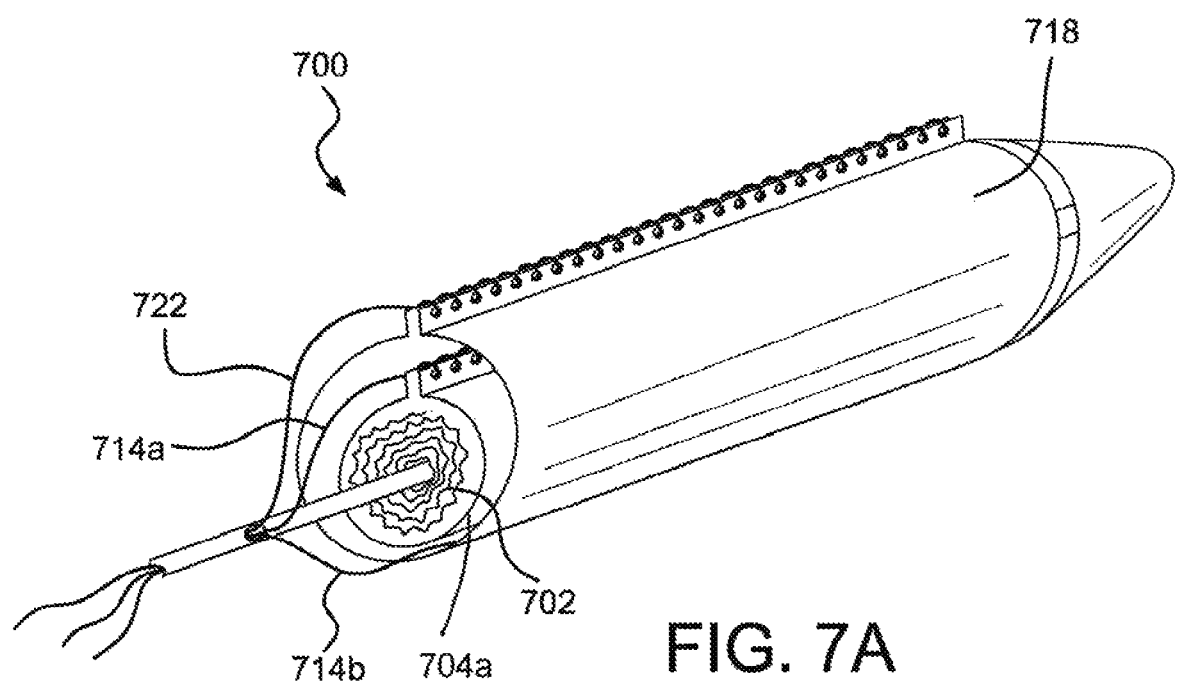
FIGS. 7A and B are, respectively, perspective and axial views of a catheter assembly having a medical device constrained in a delivery profile.
Figure 7B:
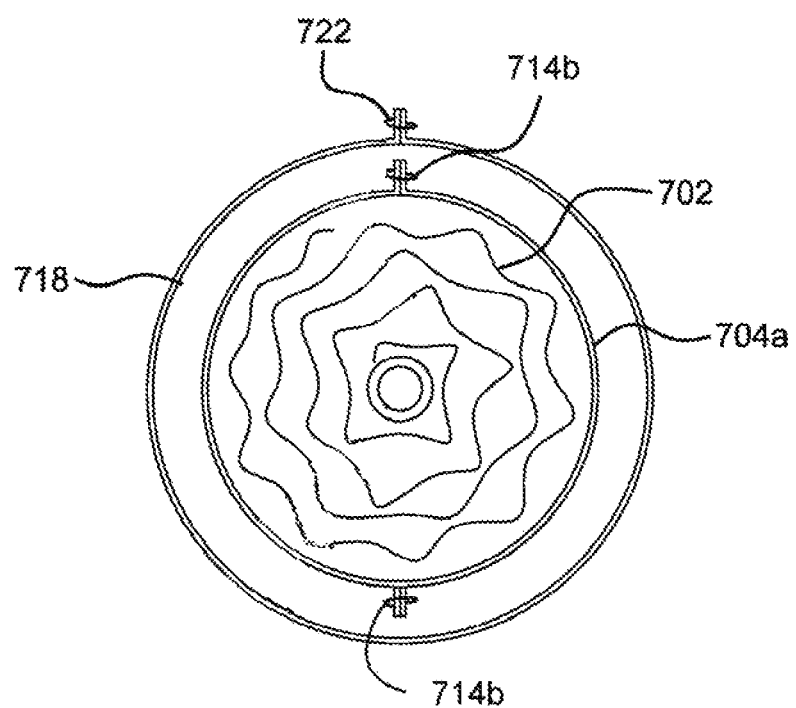
FIG. 7C is a perspective view of the catheter assembly having a medical device constrained in an intermediate configuration.
Figure 7C:
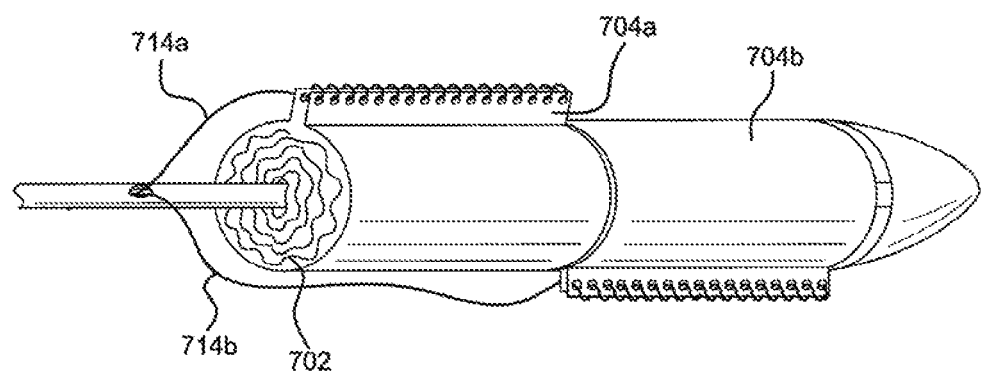

For example, with reference to FIGS. 7A-7C, a catheter assembly 700 comprises an expandable implant 702 and secondary sleeves 704a and 704b. Secondary sleeves 704a and 704b constrain expandable implant 702 to an intermediate configuration. Secondary sleeves 704a and 704b are held in position around expandable implant 702 by coupling members 714a and 714b, respectively.

Catheter assembly 700 further comprises a primary sleeve 718, which constrains expandable implant 702 in a collapsed configuration for delivery to the vasculature of a patient. Primary sleeve 718 is held in position around expandable implant 702 by primary coupling member 722.

Once expandable implant 702 is sufficiently close to the treatment area of the vasculature, primary coupling member 722 is disengaged from primary sleeve 718, which releases primary sleeve 718 and allows expanded implant 702 to expand to a larger diameter. After primary sleeve 718 has been expanded, secondary sleeves 704a and 704b constrain the expandable implant 702 in the intermediate configuration. In the intermediate configuration, expandable implant 702 may be oriented and adjusted to a final desirable location within the treatment area of the vasculature.

Figure 5A:
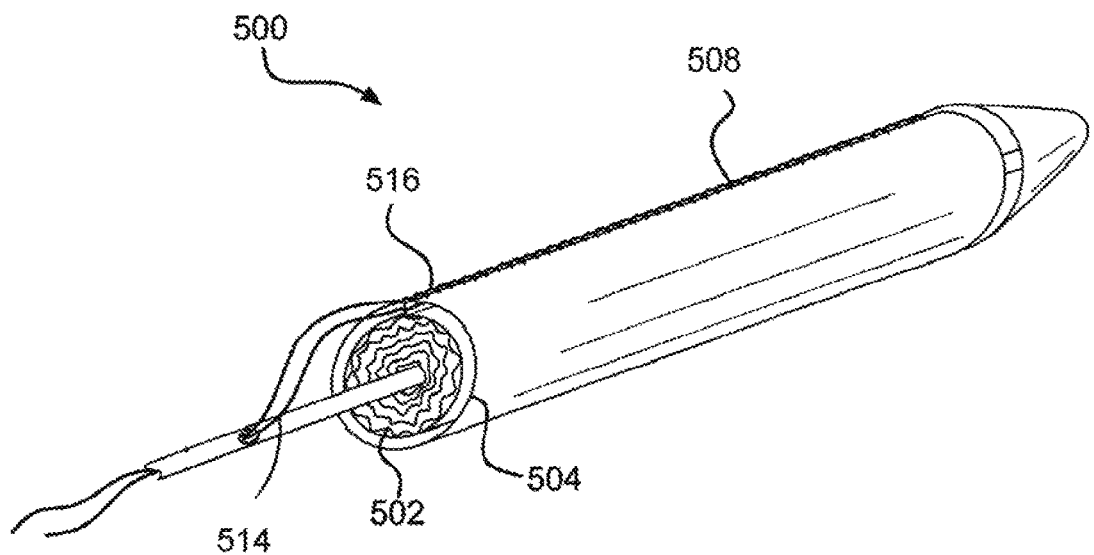
FIGS. 5A and B are, respectively, perspective and axial views of a catheter assembly having a medical device constrained in a delivery profile.
Figures 5B, 5C:
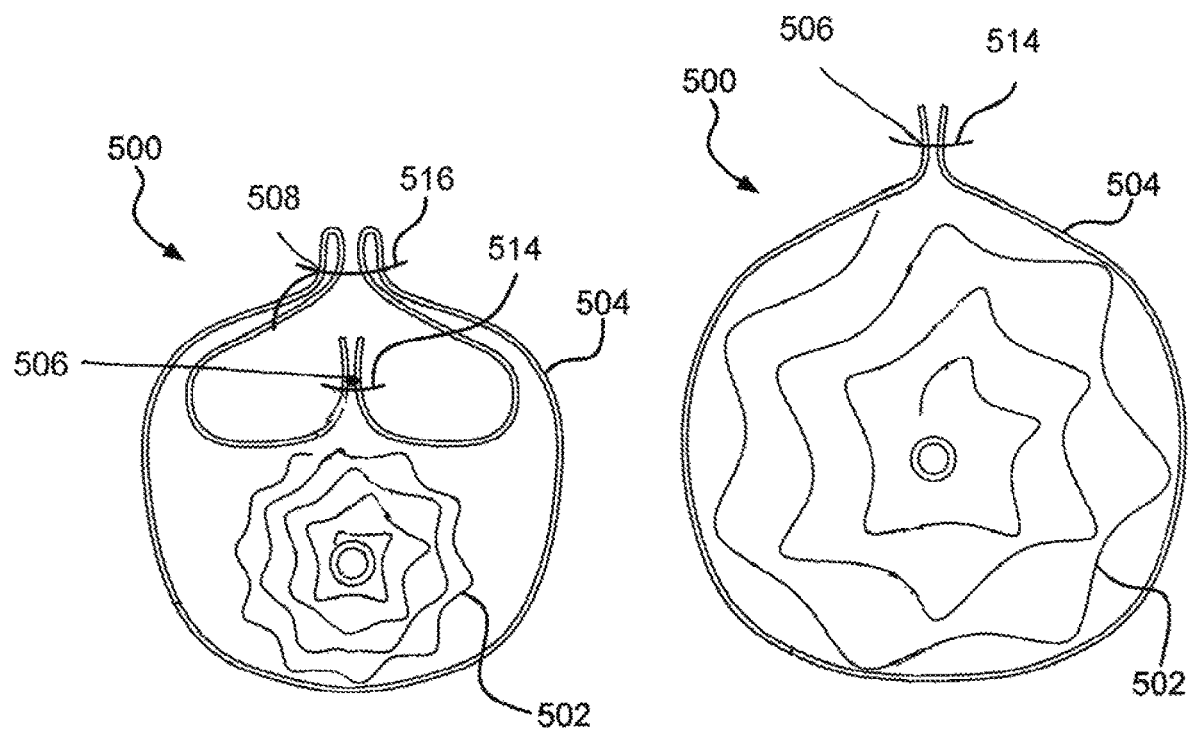
FIG. 5C is an axial view of the catheter assembly having a medical device constrained in an intermediate configuration.

In other embodiments of the present disclosure, a single sleeve may be used to constrain the expandable implant in both a collapsed configuration and an intermediate configuration. For example, with reference to FIGS. 5A-5B, catheter assembly 500 comprises an expandable implant 502, a monosleeve 504, a primary coupling member 516 and a secondary coupling member 514.

Monosleeve 504 further comprises a plurality of intermediate holes 506. In this configuration, secondary coupling member 514 is stitched or woven through intermediate holes 506, constricting monosleeve 504 and expandable implant 502 to the diameter of an intermediate configuration. In the intermediate configuration, the diameter of expandable implant 502 is less than the expanded diameter and larger than the diameter of the collapsed configuration.

Monosleeve 504 further comprises a plurality of compressed holes 508. In this configuration, primary coupling member 516 is stitched or woven through compressed holes 508, constricting monosleeve 504 and expandable implant 502 to the diameter of the collapsed configuration. The diameter of the collapsed configuration is selected to allow for delivery of the expandable implant 502 to the treatment area of the vasculature of a patient.

Once expandable implant 502 has been delivered to a region near the treatment area of the vasculature, primary coupling member 516 may be disengaged from monosleeve 504, allowing expandable implant 502 to be expanded to the intermediate configuration. Expandable implant 502 may be oriented and adjusted to a proper location within the treatment area of the vasculature. After final positioning, secondary coupling member 514 may be disengaged from monosleeve 504, and expandable implant 502 may be expanded to the expanded configuration.

Although a number of specific configurations of coupling members (for example, primary and secondary coupling members) and sleeves (for example primary and secondary sleeves) have been discussed, the use of any number and/or configuration of constraining members and sleeves is within the scope of the present disclosure.

As discussed above, various embodiments may comprise a plurality of expandable implants. In such embodiments, a single sleeve, multiple sleeves, and/or multiple concentric sleeves may be used in conjunction with the plurality of expandable implants. The use of any number of expandable implants, with any configuration of single or multiple sleeves, is within the scope of the present disclosure.

In various embodiments, sleeves used to constrain expandable implants may further comprise radiopaque markers. In such configurations, radiopaque markers may be located at the edges of sleeves, in the region where a coupling member is stitched through the series of openings. Radiopaque markers may assist in the positioning and orientation of the expandable implant within a vasculature, for example, by increasing the visibility of the location and orientation of sleeves and coupling member during the use of a radiographic device, such as an x-ray.

For example, with reference to FIG. 1, sleeve 104c may comprise a radiopaque marker (not shown). In various embodiments, the radiopaque marker comprises a circumferential band, located at or near the distal end of sleeve 104c. Any placement or configuration of a radiopaque marker which assists in the location and orientation of an expandable implant within a vasculature is within the scope of the present disclosure.

In various embodiments of the present disclosure, an expandable implant may comprise at least one target portion. In such configurations, the target portion or portions are located on the surface of the expandable implant. As noted above, in various embodiments, the target portion or portions may comprise side branch fenestrations. Side branch fenestrations allow for branching devices, such as branching stent grafts, to be connected to and in with communication the expandable implant. In various configurations, the diameter of the side branch fenestrations may be approximately the same as the vessel to be repaired. In other configurations, the diameter of the side branch fenestrations may be larger than the diameter of the vessel to be repaired. In yet other configurations, the diameter of the side branch fenestrations may be less than the diameter of the vessel to be repaired.

The cross sections of side branch fenestrations may be, for example circular, "D" shaped, oval, triangular, square, polygon shaped or randomly shaped. Side branch fenestrations of any cross-sectional shape are within the scope of the present disclosure.

In various embodiments, target portions may comprise a fenestratable portion. In such configurations, the target portions are comprised of a frangible material which may be fenestrated by an endolumenal tool after the expandable implant has been partially or completely implanted in the vasculature of a patient. Once fenestrated, the target portion may be used, for example, to install branching stent grafts to the expandable implant.

In various embodiments of the present disclosure which comprise target portions, the target portions may be oriented such that they are covered by one or more sleeves. In such configurations, the target portions may be exposed to the vasculature upon expansion of the one or more sleeves.

Figure 4:
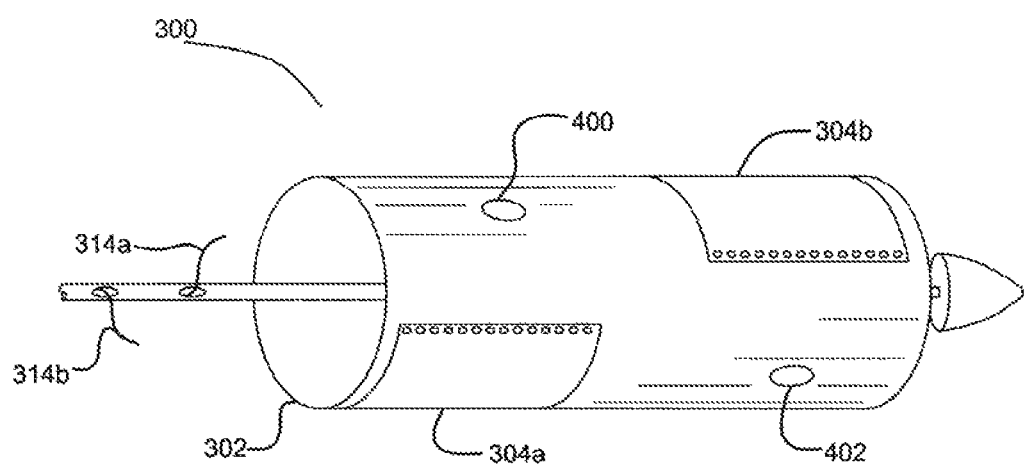
FIG. 4 is a perspective view of a catheter assembly having an expanded medical device showing the positions of the angularly displaced sleeves.

For example, with reference to FIG. 4, expandable device 300 comprises target portions 400 and 402. Target portions 400 and 402 are configured such that they are covered by sleeves 304a and 304b when the expandable implant 302 is in a collapsed configuration. Once sleeves 304a and 304b are expanded, expandable implant 302 expands to a larger diameter, exposing target portions 400 and 402 between parallel edges of the sleeves.

Figure 2:
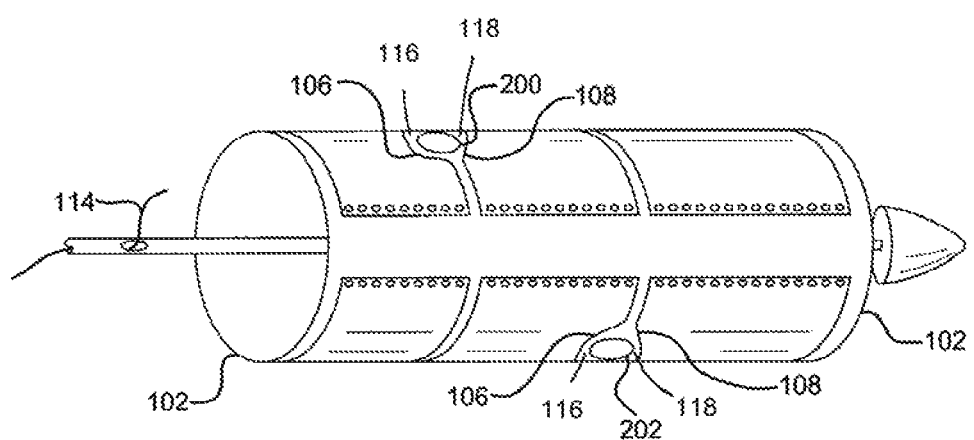
FIG. 2 is a perspective view of a catheter assembly having an expanded medical device showing the positions of the sleeves relative to side branch fenestrations of the medical device.

In other configurations, target portions may be oriented such that they are surrounded, but not covered, by multiple sleeves. For example, with reference to FIG. 2, catheter assembly 100 comprises an expandable implant 102 with target portions 200 and 202. In this embodiment, target portions 200 and 202 are positioned such that they are surrounded, and not covered, by adjacent sleeves 104a, 104b and 104c.

In such configurations, sleeves 104 may comprise lateral openings 116 and/or 118. In various embodiments, lateral openings 116 and/or 118 comprise apertures, notches or indentations at either or both ends of sleeves 104. Such apertures, notches or indentations may interact with each other to surround, but not cover, target portions 200 and/or 202.

For example, target portion 200 may be positioned between the distal end 106 of sleeve 104a and the proximal end 108 of sleeve 104b. Distal end 106 of sleeve 104a and proximal end 108 of sleeve 104b may each comprise lateral openings 116 and/or 118 which allow target portion 200 to be exposed to the vasculature of the patient upon expansion of sleeves 104a and 104b.

Further, target portion 202 may be positioned between the distal end 106 of sleeve 104b and the proximal end 108 of sleeve 104c. Distal end 106 of sleeve 104b and proximal end 108 of sleeve 104c may each comprise circular notches which allow target portion 200 to be exposed to the vasculature of the patient upon expansion of sleeves 104b and 104c.

Additionally, in various embodiments having multiple sleeves for example, to provide for collapsed, intermediate and full deployment, lateral openings may be present in each of the sleeves and located so as to allow the exposure of target portions to the vasculature at each stage of deployment. In various embodiments, the lateral openings of the primary and secondary sleeves may be of different sizes, for example, smaller on the secondary sleeve (or sleeves) and larger on the primary sleeve (or sleeves) (or vice versa).

In various embodiments, target portions may be positioned under lateral openings cut in a single sleeve. In such embodiments, the lateral openings are large enough that the single sleeve acts as multiple sleeves like those described above with regard to FIG. 2. For example, with reference to FIGS. 7A and 7B, sleeves 704a and/or 704b may comprise at least one window which is large enough and oriented such that the lateral openings are oriented over at least one target portion. Any configuration of sleeve which allows access to target portions of an expandable implant is within the scope of the present invention.

In various embodiments, expandable devices may comprise a plurality of target portions such that at least one target portion is located between adjacent sleeves and at least one target portion is located between the parallel edges of an expanded sleeve or sleeves. Any configuration of target portions, including those located between adjacent sleeves and those located between parallel edges of an expanded sleeve, are within the scope of the present disclosure.

In various embodiments of the present disclosure, the target portions may comprise radiopaque segments. In such configurations, the target portions may be surrounded by radiopaque segments or markers which assist in locating and orienting the target portions and the expandable implant within the patient's vasculature. In various embodiments, the target portions comprise both radiopaque segments and either a side branch fenestration or a fenestratable portion. In these configurations, radiopaque segments may, among other things, assist in the delivery to and installation of side branch stent grafts to the target portions.

In various embodiments, a target portion may comprise a drug eluting element. In these configurations, a drug eluting element comprises a segment which releases a therapeutic agent or drug once the target portion has been exposed to the vasculature of a patient. Examples of such therapeutic agents or drugs include prochlorperazine edisylate, ferrous sulfate, aminocaproic acid, mecaxylamine hydrochloride, procainamide hydrochloride, amphetamine sulfate, methamphetamine hydrochloride, benzphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenform in hydrochloride, methylphenidate hydrochloride, theophylline cholinate, cephalexin hydrochloride, diphenidol, meclizine hydrochloride, prochlorperazine maleate, phenoxybenzamine, thiethylperazine maleate, anisindione, diphenadione, erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, hydrocortisone, hydrocorticosterone acetate, cortisone acetate, dexamethasone and its derivatives such as betamethasone, triamcinolone, methyltestosterone, 17-.beta.-estradiol, ethinyl estradiol, ethinyl estradiol 3-methyl ether, prednisolone, 17-.beta.-hydroxyprogesterone acetate, 19-nor-progesterone, norgestrel, norethindrone, norethisterone, norethiederone, progesterone, norgesterone, norethynodrel, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, atorvastatin, simvastatin, pravastatin, fluvastatin, lovastatin, cephalexin, erythromycin, haloperidol, zomepirac, ferrous lactate, vincamine, phenoxybenzamine, diltiazem, milrinone, captropril, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captopril, ramipril, enalaprilat, famotidine, nizatidine, sucralfate, etintidine, tetratolol, minoxidil, chlordiazepoxide, diazepam, amitriptylin, and imipramine. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatropin, oxytocin, vasopressin, prolactin, somatostatin, lypressin, pancreozym in, luteinizing hormone, LHRH, interferons, interleukins, growth hormones such as human growth hormone, bovine growth hormone and porcine growth hormone, fertility inhibitors such as the prostaglandins, fertility promoters, growth factors, and human pancreas hormone releasing factor.

In various embodiments, target portions may comprise a sensor such as a temperature and/or pressure sensor. In other embodiments, the sensor may measure the rate of blood flow. Any sensor which may be implanted or connected to target portions of an expandable implant are within the scope of the invention and irrespective of the type of sensor used, sleeves may be oriented and configured such that the sensor or sensors are exposed the vasculature of the patient upon expansion and/or removal of the sleeves by structures and methods such as those disclosed herein.

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

Likewise, numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. A deployment system for an endoluminal device, the system comprising:
    an expandable endoluminal device;
    a first sleeve wrapped circumferentially about the expandable endoluminal device to maintain the endoluminal device in a collapsed configuration, the first sleeve having a first portion and a second portion, the first portion being releasably coupled to the second portion to define a first seam;
    a first coupling member releasably coupling the first and second portions of the first sleeve together; and
    a second sleeve wrapped circumferentially about the expandable endoluminal device, the second sleeve having a first portion and a second portion, the first portion of the second sleeve being releasably coupled to the second portion of the second sleeve to define a second seam that is angularly offset relative to the first seam of the first sleeve and the first releaseable sleeve defines a first releasable seam and a second releasable seam, the first releasable seam is configured to maintain the endoluminal device at the first diameter prior to release of the first releasable seam and the second releasable seam is configured to maintain the endoluminal device at the intermediate diameter prior to release of the second releasable seam.

2. The system of claim 1, wherein the second seam is hidden beneath the first seam.

3. The system of claim 1, wherein the first seam is generally parallel with a longitudinal axis of the expandable endoluminal device.

4. The system of claim 1, wherein the first seam is generally parallel to the second seam.

5. The system of claim 1, further comprising a second coupling member releasably coupling the first and second portions of the second sleeve together.

6. The system of claim 1, wherein the first and second portions of the first sleeve that are releasably coupled are first and second edges of the first sleeve.

7. The system of claim 1, wherein the second releasable seam is hidden beneath the first releasable seam.

8. The system of claim 1, wherein the first releasable seam and the second releasable seam are generally parallel with a longitudinal axis of the endoluminal device.

9. The system of claim 1, wherein the first seam is generally parallel to the second seam.

10. The system of claim 1, further comprising a first coupling member releasably securing the first releaseable seam and a second coupling member releasably securing the second releasable seam.

11. The system of claim 1, wherein the first and second releasable seams are formed by portions of the first sleeve that are releasably coupled together.

12. The system of claim 1, wherein the second releaseable sleeve is configured to maintain the endoluminal device at the intermediate diameter prior to release of the second releasable seam.

13. The system of claim 1, wherein the endoluminal device has a first portion and a second portion that is longitudinally offset from the first portion, and further wherein first releaseable sleeve is configured to maintain the first portion of the endoluminal device at the intermediate diameter and the second releaseable sleeve is configured to maintain the second portion of the endoluminal device at the intermediate diameter.

14. The system of claim 1, wherein the second releasable seam is hidden beneath the first releasable seam.

15. The system of claim 1, wherein the first releasable seam and the second releasable seam are generally parallel with a longitudinal axis of the endoluminal device.

16. The system of claim 1, wherein the first seam is generally parallel to the second seam.

17. The system of claim 1, further comprising a first coupling member releasably securing the first releaseable seam and a second coupling member releasably securing the second releasable seam.

18. A deployment system for an endoluminal device, the system comprising:
an endoluminal device transitionable from a first diameter to a second, larger diameter and from the first diameter to an intermediate diameter that is between the first and second diameters;
a first sleeve extending circumferentially about the endoluminal device, the first sleeve being secured about the endoluminal device and maintaining the endoluminal device at the first diameter, the first sleeve being releasable to deploy the device to the intermediate diameter such that the endoluminal device is maintained at the intermediate diameter with the first releasable sleeve including a first releasable seam and a second releasable seam with the first releasable seam or the second releasable seam being configured to maintain the endoluminal device at the intermediate diameter prior to release of the first releasable seam or the second releasable seam; and
a second sleeve extending circumferentially about the endoluminal device, the second sleeve being longitudinally offset along the endoluminal device relative to the first sleeve.

* * * * *